(12) United States Patent
Feldman et al.

(10) Patent No.: US 9,593,085 B2
(45) Date of Patent: Mar. 14, 2017

(54) BLUE LUMINESCENT COMPOUNDS

(71) Applicant: E I DU PONT DE NEMOURS AND COMPANY, Wilmington, DE (US)

(72) Inventors: Jerald Feldman, Wilmington, DE (US); Stephan James McLain, Wilmington, DE (US); Ying Wang, West Chester, PA (US)

(*) Notice: Subject to any disclaimer, the term of this patent is extended or adjusted under 35 U.S.C. 154(b) by 0 days.

(21) Appl. No.: 14/383,138

(22) PCT Filed: Apr. 2, 2013

(86) PCT No.: PCT/US2013/034934
§ 371 (c)(1),
(2) Date: Sep. 5, 2014

(87) PCT Pub. No.: WO2013/151989
PCT Pub. Date: Oct. 10, 2013

(65) Prior Publication Data
US 2015/0014675 A1 Jan. 15, 2015

Related U.S. Application Data

(60) Provisional application No. 61/619,063, filed on Apr. 2, 2012.

(51) Int. Cl.
| | | |
|---|---|---|
| C07D 249/08 | (2006.01) | |
| C07F 15/00 | (2006.01) | |
| C09K 11/06 | (2006.01) | |
| H01L 51/00 | (2006.01) | |
| H01L 51/50 | (2006.01) | |

(52) U.S. Cl.
CPC ........ C07D 249/08 (2013.01); C07F 15/0033 (2013.01); C09K 11/06 (2013.01); H01L 51/0085 (2013.01); *C09K 2211/1007* (2013.01); *C09K 2211/1011* (2013.01); *C09K 2211/1059* (2013.01); *C09K 2211/185* (2013.01); *H01L 51/5016* (2013.01); *H01L 51/5024* (2013.01)

(58) Field of Classification Search
CPC .................... C07D 249/08; C07F 15/0033
See application file for complete search history.

(56) References Cited

U.S. PATENT DOCUMENTS

| | | |
|---|---|---|
| 6,670,645 B2 | 12/2003 | Grushin et al. |
| 6,875,524 B2 | 4/2005 | Hatwar et al. |
| 7,659,010 B2 | 2/2010 | Burn et al. |
| 7,915,415 B2 | 3/2011 | Knowles et al. |
| 2004/0102577 A1 | 5/2004 | Hsu et al. |
| 2004/0127637 A1 | 7/2004 | Hsu et al. |
| 2005/0158577 A1 | 7/2005 | Ishibashi et al. |
| 2005/0205860 A1 | 9/2005 | Hsu et al. |
| 2007/0009759 A1* | 1/2007 | Burn .................. C07F 15/0033 428/690 |
| 2012/0074390 A1* | 3/2012 | Seo ...................... C07D 405/04 257/40 |

FOREIGN PATENT DOCUMENTS

| | | |
|---|---|---|
| JP | 2008210941 A * | 9/2008 |
| WO | 03/008424 A1 | 1/2003 |
| WO | 03/040257 A1 | 5/2003 |
| WO | 03/063555 A1 | 7/2003 |
| WO | 03/091688 A2 | 11/2003 |
| WO | 2004/016710 A1 | 2/2004 |
| WO | 2009/018009 A1 | 2/2009 |
| WO | 2009/067419 A1 | 5/2009 |

OTHER PUBLICATIONS

Shih-Chun Lo et al, "Blue Phosphorescence From Iridium (III) Complexes at Room Temperature", Chemical Materials, 2006, V. 18, pp. 5119-5129.
Lixin Xiao et al, "Recent Progresses on Materials for Electrophosphorescent Organic Light-Emitting Devices", Advanced Materials, 2011, 23, pp. 926-952.
G. Gustafsson et al, "Flexible Light-Emitting Diodes Made From Soluble Conducting Polymers", Nature, vol. 357, Jun. 11, 1992, pp. 477-479.
PCT Search Report, Application No. PCT/US2013/034934, dated Jul. 26, 2013.

* cited by examiner

*Primary Examiner* — Joseph Kosack (57) ABSTRACT

There is provided a compound having Formula I

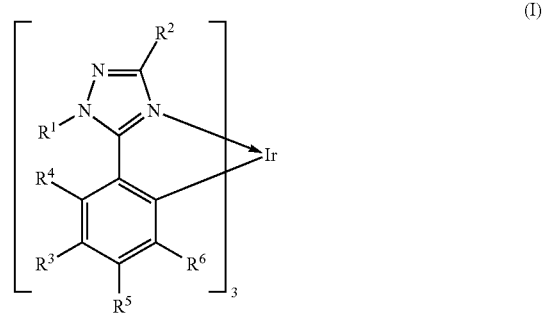

In the formula: $R^1$ can be alkyl, aryl, alkylaryl, or deuterated analogs thereof; $R^2$ can be alkyl or deuterated alkyl; $R^3$ can be H, D, aryl, or deuterated aryl; and $R^4$-$R^6$ are the same or different and can be H, D, alkyl, or deuterated alkyl. In the formula, at least one of the following conditions is met:
  (i) $R^1$ is a secondary alkyl, a tertiary alkyl, aryl, alkylaryl, or deuterated analog thereof;
  (ii) $R^3$ is aryl or deuterated aryl;
  (iii) at least one of $R^3$-$R^6$ is D.

4 Claims, 2 Drawing Sheets

BLUE LUMINESCENT COMPOUNDS

RELATED APPLICATION DATA

This application claims priority under 35 U.S.C. §119(e) from U.S. Provisional Application No. 61/619,063, filed on Apr. 2, 2012, which is incorporated by reference herein in its entirety.

BACKGROUND INFORMATION

Field of the Disclosure

This disclosure relates in general to blue luminescent compounds and their use in electronic devices.

Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. Metal complexes, particularly iridium and platinum complexes are also known to show electroluminescence. In some cases these small molecule compounds are present as a dopant in a host material to improve processing and/or electronic properties.

There is a continuing need for new luminescent compounds.

SUMMARY

There is provided a material having Formula I (I)

wherein:
  $R^1$ is selected from the group consisting of alkyl, aryl, alkylaryl, and deuterated analogs thereof;
  $R^2$ is selected from the group consisting of alkyl, and deuterated alkyl;
  $R^3$ is selected from the group consisting of H, D, aryl, and deuterated aryl; and
  $R^4$-$R^6$ are the same or different and are selected from the group consisting of H, D, alkyl, and deuterated alkyl;
with the proviso that at least one of the following conditions is met:

(i) $R^1$ is selected from the group consisting of a secondary alkyl, a tertiary alkyl, aryl, alkylaryl, and deuterated analogs thereof;
  (ii) $R^3$ is selected from the group consisting of aryl and deuterated aryl;
  (iii) at least one of $R^3$-$R^6$ is D.

There is also provided an organic electronic device comprising a first electrical contact, a second electrical contact and a photoactive layer therebetween, the photoactive layer comprising the material having Formula I.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Material Having Formula I, Synthesis, Devices, and finally Examples.

1. Definitions and Clarification of Terms

Before addressing details of embodiments described below, some terms are defined or clarified.

The term "alkyl" is intended to mean a group derived from an aliphatic hydrocarbon and includes a linear, a branched, or a cyclic group. In some embodiments an alkyl has from 1-20 carbon atoms.

The term "anti-quenching" when referring to a layer or material, refers to such layer or material which prevents quenching of blue luminance by the electron transport layer, either via an energy transfer or an electron transfer process.

The term "aromatic compound" is intended to mean an organic compound comprising at least one unsaturated cyclic group having delocalized pi electrons.

The term "aryl" is intended to mean a group derived from an aromatic hydrocarbon having one point of attachment. The term includes groups which have a single ring and those which have multiple rings which can be joined by a single bond or fused together. The term is intended to include heteroaryls. The term "alkylaryl" is intended to mean an aryl group having one or more alkyl substituents.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" is intended to mean that at least one H has been replaced by D. The term "deuterated analog" refers to a structural analog of a compound or group in which one or more available hydrogens have been replaced with deuterium. In a deuterated compound or deuterated analog, the deuterium is present in at least 100 times the natural abundance level.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The prefix "hetero" indicates that one or more carbon atoms have been replaced with a different atom. In some embodiments, the different atom is N, O, or S.

The term "host material" is intended to mean a material, usually in the form of a layer, to which a dopant may be added. The host material may or may not have electronic characteristic(s) or the ability to emit, receive, or filter radiation.

The terms "luminescent material" and "emitter" are intended to mean a material that emits light when activated by an applied voltage (such as in a light-emitting diode or light-emitting electrochemical cell). The term "blue luminescent material" is intended to mean a material capable of emitting radiation that has an emission maximum at a wavelength in a range of approximately 445-490 nm. The term "green luminescent material" is intended to mean a material capable of emitting radiation that has an emission maximum at a wavelength in a range of approximately 495-570 nm. The term "orange luminescent material" is intended to mean a material capable of emitting radiation that has an emission maximum at a wavelength in a range of approximately 590-620 nm. The term "red luminescent material" is intended to mean a material capable of emitting radiation that has an emission maximum at a wavelength in a range of approximately 620-750 nm. The term "yellow luminescent material" is intended to mean a material capable of emitting radiation that has an emission maximum at a wavelength in a range of approximately 570-590 nm.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell).

The term "secondary alkyl" refers to an alkyl group that is attached via a carbon which is bonded to two other carbons. Secondary alkyls including monocyclic alkyls.

The term "tertiary alkyl" refers to an alkyl group that is attached via a carbon which is bonded to three other carbons.

All groups may be unsubstituted or substituted. The substituent groups are discussed below.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, $81^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic cell, and semiconductive member arts.

2. Compounds Having Formula I

The new compounds described herein have Formula I (I)

wherein:
- $R^1$ is selected from the group consisting of alkyl, aryl, alkylaryl, and deuterated analogs thereof;
- $R^2$ is selected from the group consisting of alkyl, and deuterated alkyl;
- $R^3$ is selected from the group consisting of H, D, aryl, and deuterated aryl; and
- $R^4$-$R^6$ are the same or different and are selected from the group consisting of H, D, alkyl, and deuterated alkyl;

with the proviso that at least one of the following conditions is met:
- (i) $R^1$ is selected from the group consisting of a secondary alkyl, a tertiary alkyl, aryl, alkylaryl, and deuterated analogs thereof;
- (ii) $R^3$ is selected from the group consisting of aryl and deuterated aryl;
- (iii) at least one of $R^3$-$R^6$ is D.

In some embodiments, the compounds having Formula I are useful as emissive materials. In some embodiments, the compounds are blue emissive materials. They can be used alone or as a dopant in a host material.

The compounds having Formula I are soluble in many commonly used organic solvents. Solutions of these compounds can be used for liquid deposition using techniques such as discussed above. Unexpectedly, it has been found that the compounds having the substitution pattern shown in Formula I have improved efficiencies in devices. This is advantageous for reducing energy consumption in all types of devices, and particularly for lighting applications. Higher efficiency also improves device lifetime at constant luminance.

Specific embodiments of the present invention include, but are not limited to, the following.

Embodiment 1

The compound of Formula I, wherein the compound is deuterated.

Embodiment 2

The compound of Formula I, wherein the compound is at least 10% deuterated. By "% deuterated" or "% deuteration" is meant the ratio of deuterons to the total of hydrogens plus deuterons, expressed as a percentage. The deuteriums may be on the same or different groups.

Embodiment 3

The compound of Formula I, wherein the compound is at least 25% deuterated.

Embodiment 4

The compound of Formula I, wherein the compound is at least 50% deuterated.

Embodiment 5

The compound of Formula I, wherein the compound is at least 75% deuterated.

Embodiment 6

The compound of Formula I, wherein the compound is at least 90% deuterated.

Embodiment 7

The compound of Formula I, wherein $R^1$ is a secondary alkyl or deuterated secondary alkyl having 3-20 carbons.

Embodiment 8

The compound of Formula I, wherein $R^1$ is a secondary alkyl or deuterated secondary alkyl having 3-12 carbons.

Embodiment 9

The compound of Formula I, wherein $R^1$ is a secondary alkyl or deuterated secondary alkyl having 5-8 carbons.

Embodiment 10

The compound of Formula I, wherein $R^1$ is selected from the group consisting of 2-propyl, 2-butyl, 2-pentyl, cyclohexyl, methylcyclohexyl, and deuterated analogs thereof.

Embodiment 11

The compound of Formula I, wherein $R^1$ is a tertiary alkyl or deuterated tertiary alkyl having 4-20 carbons

Embodiment 12

The compound of Formula I, wherein $R^1$ is a tertiary alkyl or deuterated tertiary alkyl having 4-12 carbons.

Embodiment 13

The compound of Formula I, wherein $R^1$ is selected from the group consisting of t-butyl, t-pentyl, 1-methylcyclohexyl, 1-adamantyl, and deuterated analogs thereof.

Embodiment 14

The compound of Formula I, wherein $R^1$ is an aryl or deuterated aryl having 6-20 carbons

Embodiment 15

The compound of Formula I, wherein $R^1$ is an aryl or deuterated aryl having 6-12 carbons.

Embodiment 16

The compound of Formula I, wherein $R^1$ is selected from the group consisting of phenyl, biphenyl, napthyl, and deuterated analogs thereof, wherein any of the previous groups may have one or more substituents that are alkyl groups with 1-10 carbons.

Embodiment 17

The compound of Formula I, wherein $R^1$ is selected from the group consisting of phenyl, tolyl, xylyl, mesityl, and deuterated analogs thereof.

Embodiment 18

The compound of Formula I, wherein $R^2$ is an alkyl or deuterated alkyl having 1-20 carbons

Embodiment 19

The compound of Formula I, wherein $R^2$ is an alkyl or deuterated alkyl having 1-12 carbons.

Embodiment 20

The compound of Formula I, wherein $R^2$ is an alkyl or deuterated alkyl having 3-8 carbons.

Embodiment 21

The compound of Formula I, wherein $R^2$ is selected from the group consisting of methyl, propyl, butyl, and deuterated analogs thereof.

Embodiment 22

The compound of Formula I, wherein $R^3$ is H or D.

Embodiment 23

The compound of Formula I, wherein $R^3$ is an aryl or deuterated aryl group having 6-30 carbons.

Embodiment 24

The compound of Formula I, wherein $R^3$ is selected from the group consisting of phenyl, biphenyl, naphthyl, and deuterated analogs thereof, wherein any of the previous groups may have one or more substituents that are alkyl groups with 1-10 carbons.

Embodiment 25

The compound of Formula I, wherein $R^4$ is H or D.

Embodiment 26

The compound of Formula I, wherein $R^4$ is selected from the group consisting of an alkyl having 1-10 carbons and a deuterated alkyl having 1-10 carbons.

Embodiment 27

The compound of Formula I, wherein $R^5$ is H or D.

Embodiment 28

The compound of Formula I, wherein $R^5$ is selected from the group consisting of an alkyl having 1-10 carbons and a deuterated alkyl having 1-10 carbons.

Embodiment 29

The compound of Formula I, wherein $R^6$ is H or D.

Embodiment 30

The compound of Formula I, wherein $R^6$ is selected from the group consisting of an alkyl having 1-10 carbons and a deuterated alkyl having 1-10 carbons.

Embodiment 31

The compound of Formula I, wherein $R^4$-$R^6$ are selected from H and D.

Embodiment 32

The compound of Formula I, wherein $R^3$-$R^6$ are all D.

Embodiment 33

The compound of Formula I, wherein one of $R^3$-$R^6$ is an alkyl or deuterated alkyl having 1-20 carbons, and the others of $R^3$-$R^6$ are H or D. I

Embodiment 34

The compound of Embodiment 33, wherein the alkyl or deuterated alkyl has 1-10 carbons.

Embodiment 35

The compound of Formula I, wherein two of $R^3$-$R^6$ are the same or different and are an alkyl or deuterated alkyl having 1-20 carbons, and two of $R^3$-$R^6$ are H or D.

Embodiment 36

The compound of Embodiment 35, wherein the alkyl or deuterated alkyl has 1-10 carbons.

Embodiment 37

The compound of Formula I, wherein three of $R^3$-$R^6$ are the same or different and are an alkyl or deuterated alkyl having 1-20 carbons, and one of $R^3$-$R^6$ is H or D.

Embodiment 38

The compound of Embodiment 37, wherein the alkyl or deuterated alkyl has 1-10 carbons.

Embodiment 39

The compound of Formula I, wherein $R^3$-$R^6$ are the same or different and are an alkyl or deuterated alkyl having 1-20 carbons.

Embodiment 40

The compound of Embodiment 39, wherein the alkyl or deuterated alkyl has 1-10 carbons.

Embodiment 41

The compound of Formula wherein $R^1$ is selected from the group consisting of secondary alkyls and deuterated analogs thereof, and $R^3$ is an aryl group.

Embodiment 42

The compound of Formula I, wherein $R^1$ and $R^3$ are the same or different and are aryl groups or deuterated aryl groups.

Embodiment 43

The compound of Formula I, wherein $R^1$ is selected from the group consisting of secondary alkyls and deuterated analogs thereof, and $R^3$-$R^6$ are all D.

Any of the above embodiments can be combined with one or more of the other embodiments, so long as they are not mutually exclusive. For example, the embodiment in which $R^1$ is a secondary alkyl or deuterated secondary alkyl having 3-20 carbons can be combined with the embodiment in which $R^2$ is selected from the group consisting of methyl, propyl, butyl, and deuterated analogs thereof. The same is true for the other non-mutually-exclusive embodiments discussed above. The skilled person would understand which embodiments were mutually exclusive and would thus readily be able to determine the combinations of embodiments that are contemplated by the present application.

Examples of compounds having Formula I include, but are not limited to, compounds B1 through B12 shown below.

B1

B2

B3

B4

B5

B6

B7

B8 coupling agent affords a acylated amidine; this was then reacted with a hydrazine (either the free hydrazine or the corresponding hydrochloride) to afford the 1,2,4-triazole. By using an aromatic carboxylic acid or amidine, an aryl-substituted triazole suitable for metallation/coordination by Ir(III) was obtained.

HATU = 2-(7-Aza-1H-Benzotriazole-1-yl)-1,1,3,3-tetramethyluronium hexafluorophosphate
DIPEA = Diisopropylethylamine
DMF = Dimethylforamide
$R^1$ and/or $R^2$ = substituted aromatic group A variation on this procedure is to synthesize the benzoyl acetamidine (Chua, S.; Cook, M. J.; Katritzky, A. R. *J. C. S. Perkin II*, 1974, 546.) and then react this intermediate with the hydrazine hydrochloride in a second step to give the desired 1,2,4-triazole ligand.

3. Synthesis 1,3,5-trisubstituted 1,2,4-triazole ligands were prepared from carboxylic acids, primary amidines, and monosubstituted hydrazines using a known synthetic procedure outlined below (Castanedo, G. M.; Seng, P. S.; Blaquiere, N.; Trapp, S.; Staben, S. T. *J. Org. Chem.* 2011, 76, 1177). Reaction of a carboxylic acid with an amidine in the presence of a coupling agent affords a acylated amidine; this was then The aforementioned ligands were complexed to Ir(III) by a three-step synthesis shown below. The three steps involved, first, formation of the "$L_2IrCl$ dimer," by reaction of iridium(III) chloride hydrate with excess ligand in a heated mixture of 2-ethoxyethanol and water. Next, the iridium triflate was prepared, again in high yield, by reaction of the $L_2IrCl$ dimer with silver triflate. Finally, the iridium triflate is reacted with excess ligand in refluxing 2-ethoxyethanol to afford the cyclometallated IrL₃ compound as the fac-isomer.

4. Devices

Organic electronic devices that may benefit from having one or more layers comprising the compounds having Formula I described herein include, but are not limited to, (1) devices that convert electrical energy into radiation (e.g., a light-emitting diode, light emitting diode display, lighting device, lumina ire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode).

Figure 1:
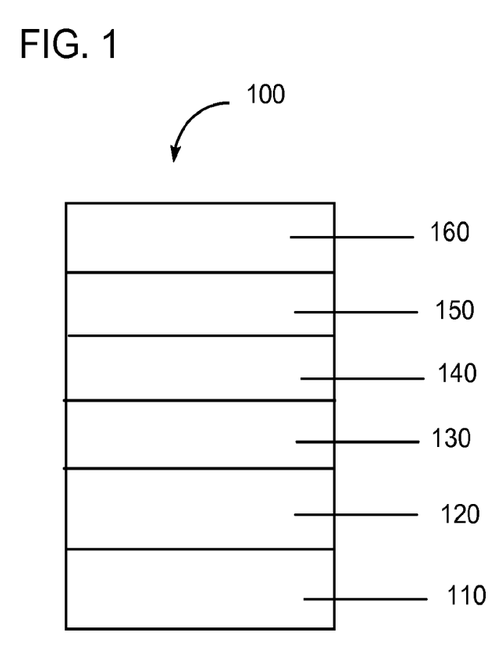
FIG. 1 includes an illustration of an organic light-emitting device.

One illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, comprising hole transport material.

Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. As a further option, devices may have an anti-quenching layer (not shown) between the photoactive layer 140 and the electron transport layer 150.

Layers 120 through 150, and any additional layers between them, are individually and collectively referred to as the active layers.

Figure 2:
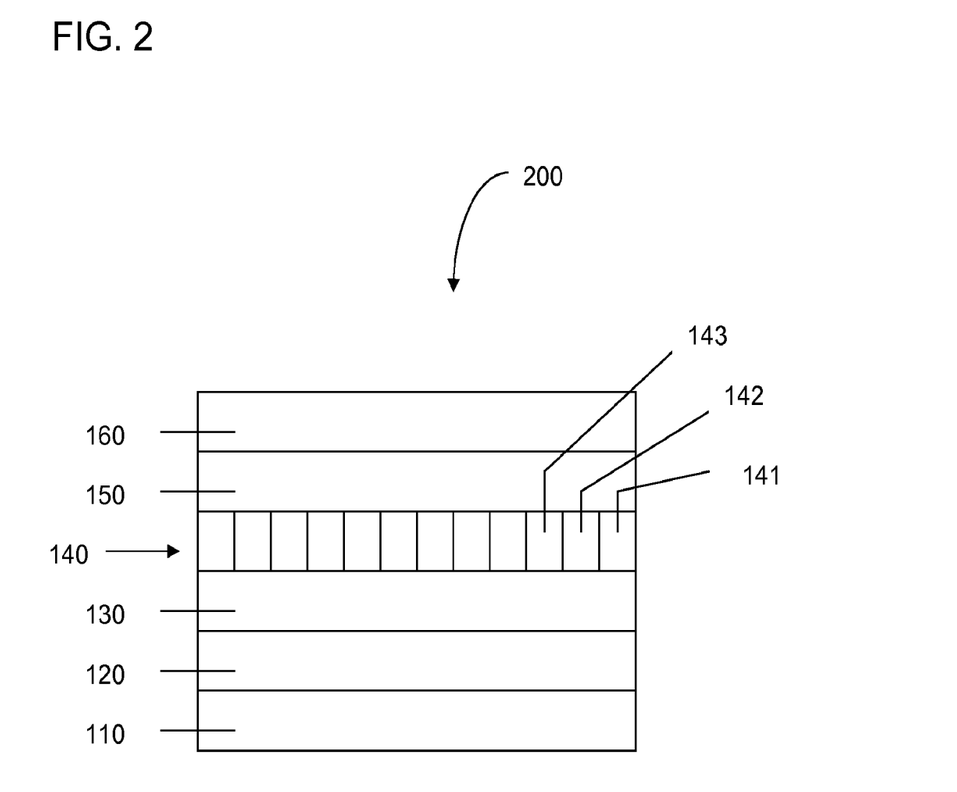
FIG. 2 includes another illustration of an organic light-emitting device.

In some embodiments, the photoactive layer is pixellated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In one embodiment, the different layers have the following range of thicknesses: anode 110, 500-5000 Å, in one embodiment 1000-2000 Å; hole injection layer 120, 50-2000 Å, in one embodiment 200-1000 Å; hole transport layer 120, 50-2000 Å, in one embodiment 200-1000 Å; photoactive layer 130, 10-2000 Å, in one embodiment 100-1000 Å; layer 140, 50-2000 Å, in one embodiment 100-1000 Å; cathode 150, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula are useful as the emissive material in photoactive layer 140, having blue emission color. They can be used alone or as a dopant in a host material.

a. Photoactive Layer

In some embodiments, the photoactive layer comprises a host material and a compound having Formula I as a dopant. In some embodiments, a second host material may be present. In some embodiments, the photoactive layer consists essentially of a host material and a compound having Formula I as a dopant. In some embodiments, the photoactive layer consists essentially of a first host material, a second host material, and a compound having Formula I as a dopant. The weight ratio of dopant to total host material is in the range of 5:95 to 70:30; in some embodiments, 10:90 to 20:80.

In some embodiments, the host has a triplet energy level higher than that of the dopant, so that it does not quench the emission. In some embodiments, the host is selected from the group consisting of carbazoles, indolocarbazoles, triazines, aryl ketones, phenylpyridines, pyrimidines, phenanthrolines, triarylamines, deuterated analogs thereof, combinations thereof, and mixtures thereof.

In some embodiments, the photoactive layer is intended to emit white light. In some embodiments, the photoactive layer comprises a host, a compound of Formula I, and one or more additional dopants emitting different colors, so that the overall emission is white. In some embodiments, the photoactive layer consists essentially of a host, a first dopant having Formula I, and a second dopant, where the second dopant emits a different color than the first dopant. In some embodiments, the emission color of the second dopant is yellow. In some embodiments, the photoactive layer consists essentially of a host, a first dopant having Formula I, a second dopant, and a third dopant. In some embodiments, the emission color of the second dopant is red and the emission color of the third dopant is green.

Any kind of electroluminescent ("EL") material can be used as second and third dopants. EL materials include, but are not limited to, small molecule organic fluorescent compounds, luminescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, arylamino derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Examples of red, orange and yellow light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

In some embodiments, the second and third dopants are cyclometallated complexes of Ir or Pt.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole injection layer 120 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (□-NPB), and porphyrinic compounds, such as copper phthalocyanine. In some embodiments, the hole transport layer comprises a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further comprises a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

Examples of electron transport materials which can be used or layer 150 include, but are not limited to, metal chelated oxinoid compounds, including metal quinolate derivatives such as tris(8-hydroxyquinolato)aluminum (AlQ)), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri (phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

An anti-quenching layer may be present between the photoactive layer and the electron transport layer to prevent quenching of blue luminance by the electron transport layer. To prevent energy transfer quenching, the triplet energy of the anti-quenching material has to be higher than the triplet energy of the blue emitter. To prevent electron transfer quenching, the LUMO level of the anti-quenching material has to be shallow enough (with respect to the vacuum level) such that electron transfer between the emitter exciton and the anti-quenching material is endothermic. Furthermore, the HOMO level of the anti-quenching material has to be deep enough (with respect to the vacuum level) such that electron transfer between the emitter exciton and the anti-quenching material is endothermic. In general, anti-quenching material is a large band-gap material with high triplet energy.

Examples of materials for the anti-quenching layer include, but are not limited to, triphenylene, triphenylene derivatives, carbazole, carbazole derivatives, and deuterated analogs thereof. Some specific materials include those shown below.

-continued

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. The hole injection material can be present in the liquid medium in an amount from 0.5 to 10 percent by weight. The hole injection layer can be applied by any continuous or discontinuous liquid deposition technique. In one embodiment, the hole injection layer is applied by spin coating. In one embodiment, the hole injection layer is applied by ink jet printing. In one embodiment, the hole injection layer is applied by continuous nozzle printing. In one embodiment, the hole injection layer is applied by slot-die coating. After liquid deposition, the liquid medium can be removed in air, in an inert atmosphere, or by vacuum, at room temperature or with heating.

The hole transport layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In one embodiment, the hole transport layer is applied by spin coating. In one embodiment, the hole transport layer is applied by ink jet printing. In one embodiment, the hole transport layer is applied by continuous nozzle printing. In one embodiment, the hole transport layer is applied by slot-die coating. After liquid deposition, the liquid medium can be removed in air, in an inert atmosphere, or by vacuum, at room temperature or with heating.

The photoactive layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic solvent is selected from chloroform, dichloromethane, toluene, anisole, 2-butanone, 3-pentanone, butyl acetate, acetone, xylene, mesitylene, chlorobenzene, tetrahydrofuran, diethyl ether, trifluorotoluene, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In one embodiment, the photoactive layer is applied by spin coating. In one embodiment, the photoactive layer is applied by ink jet printing. In one embodiment, the photoactive layer is applied by continuous nozzle printing. In one embodiment, the photoactive layer is applied by slot-die coating. After liquid deposition, the liquid medium can be removed in air, in an inert atmosphere, or by vacuum, at room temperature or with heating.

The electron transport layer can be deposited by any vapor deposition method. In one embodiment, it is deposited by thermal evaporation under vacuum.

The electron injection layer can be deposited by any vapor deposition method. In one embodiment, it is deposited by thermal evaporation under vacuum.

The cathode can be deposited by any vapor deposition method. In one embodiment, it is deposited by thermal evaporation under vacuum.

EXAMPLES

The concepts described herein will be further described in the following examples, which do not limit the scope of the invention described in the claims.

Synthesis Example 1

This example illustrates the preparation of compound B1.

Step 1. Preparation of
1-cyclohexyl-3-methyl-5-phenyl-1H-1,2,4-triazole

Benzoic acid (1.71 g, 14.0 mmol) was dissolved in anhydrous DMF (50 mL). To this stirred solution was added 2-(7-Aza-1H-Benzotriazole-1-yl)-1,1,3,3-tetramethyluronium hexafluorophosphate (5.85 g, 15.4 mmol) followed by acetamidine hydrochloride (1.97 g, 20.8 mmol) and diisopropylethylamine (7.17 g, 55.4 mmol). The resulting clear yellow solution was stirred under nitrogen for 68 h at room temperature. Cyclohexylhydrazine hydrochloride (3.16 g, 21.0 mmol) was then added, followed by acetic acid (8.0 mL). The resulting mixture was heated to 90° C. for 3 h. After cooling to room temperature, the mixture was diluted with 300 mL of ethyl acetate and stirred with excess aqueous sodium bicarbonate. The organic layer was separated and the aqueous layer extracted again with ethyl acetate. The organic layers were combined and washed three times with water, dried ($MgSO_4$), and concentrated under vacuum to afford 3.76 g of a viscous yellow oil. The sample was loaded onto a 340 g Biotage® silica gel column from ethyl acetate and eluted with a gradient of 12-100% ethyl acetate in hexane to give 2.41 g of a colorless oil (71% yield). $^1$H NMR (500 MHz, $CD_2Cl_2$) δ 1.25-2.05 (m, 10H), 2.35 (s, 3H), 4.17 (m, 1H), 7.49-7.57 (m, 5H).

Step 2. Preparation of the [$L_2IrCl$]$_2$ Compound

Combined $IrCl_3(H_2O)_3$ (0.32 g, 0.90 mmol) and 4 mL water and stirred to dissolve. Added 1-cyclohexyl-3-methyl-5-phenyl-1H-1,2,4-triazole (0.54 g, 2.24 mmole) and 13 mL of 2-ethoxyethanol, purged the mixture with nitrogen, and heated overnight at reflux. The mixture was cooled and 11 mL of water was added to help precipitate the product. The mixture was stirred for 0.5 h and then the solids were collected by filtration and washed on the filter 3× with 10 mL of water and air dried to afford a yellow solid. The solid was dried overnight under high vacuum to afford 0.59 g of a yellow solid (92% yield). $^1$H NMR (500 MHz, $CD_2Cl_2$) δ 1.39-2.30 (m, 13H), 4.76 (m, 1H), 6.19 (d, 1H), 6.70 (t, 1H), 6.87 (t, 1H), 7.46 (d, 1H).

Step 3. Preparation of the $L_2Ir(OTf)$ Compound

The [$L_2IrCl$]$_2$ compound from step 2 (0.30 g, 0.21 mmol) was dissolved in 25 mL dichloromethane. Silver trifluoromethanesulfonate (0.11 g, 0.42 mmol) was added and the mixture was stirred at room temperature 3 days. During this time, AgCl was observed to very slowly precipitate. The reaction mixture was filtered through a medium frit funnel and the yellow filtrate concentrated to dryness to afford 0.38 g of a yellow solid (quantitative yield). $^1$H NMR (500 MHz. $CD_2Cl_2$) showed broad peaks: δ 1.5-2.2 (m, 10H), 2.5 (s, 3H), 4.7 (m, 1H), 6.2 (br m, 1H), 6.6 (t, 1H), 6.8 (t, 1H), 7.3 (d, 1H).

Step 4. Preparation of the $IrL_3$ Compound

The $L_2Ir(OTf)$ compound from step 3 (0.48 g, 0.58 mmol) was dissolved in 2-ethoxyethanol (15 mL). To this stirred solution was added the ligand 1-cyclohexyl-3-methyl-5-phenyl-1H-1,2,4-triazole (0.21 g, 0.88 mmol). The reaction mixture was heated to 120° C. and stirred for 4 h. A yellow precipitate formed gradually. It was then cooled to room temperature and the precipitate filtered off and washed several times with pentane. It was dried under vacuum to afford 0.15 g of a yellow solid (yield=26%). This material was combined with the crude product from a second reaction run on twice the scale (0.38 g, 35% yield) to give a total of 0.53 g of crude product. The combined product was purified by chromatography on a 50 g Biotage® silica gel column. The sample was loaded on the column from dichloromethane and eluted with a gradient of 5-40% ethyl acetate in hexane. The product precipitated from the most concentrated fractions and was isolated by filtration and dried to afford 0.385 g of compound B1 as a fluffy yellow solid. $^1$H NMR (500 MHz, $CD_2Cl_2$) δ 1.25-2.15 (m, 13H), 4.62 (m, 1H), 6.67 (d, 1H), 6.76 (t, 1H), 6.93 (t, 1H), 7.53 (d, 1H). UPLC in isopropanol/water indicated a purity of 99.95%.

Synthesis Example 2

This example illustrates the preparation of compound B2.

Step 1. Preparation of 1-cyclohexyl-3-methyl-5-phenyl-1H-1,2,4-triazole-d$_5$

Benzoic acid-d$_5$ (5.00 g, 39.3 mmol) was dissolved in anhydrous DMF (140 mL). To this stirred solution was added 2-(7-Aza-1H-Benzotriazole-1-yl)-1,1,3,3-tetramethyluronium hexafluorophosphate (16.4 g, 43.2 mmol) followed by acetamidine hydrochloride (5.58 g, 59.0 mmol) and diisopropylethylamine (20.1 g, 156.0 mmol). The resulting clear yellow solution was stirred under nitrogen for 92 h at room temperature. Cyclohexylhydrazine hydrochloride (8.89 g, 59.0 mmol) was then added, followed by acetic acid (22.5 mL). The resulting mixture was heated to 90° C. for 5 h. After cooling to room temperature, the mixture was diluted with 750 mL of ethyl acetate and stirred with excess aqueous sodium bicarbonate. The organic layer was separated and the aqueous layer extracted again with ethyl acetate. The organic layers were combined and washed three times with water, dried (MgSO$_4$), and concentrated under vacuum to afford 12.2 g of a viscous yellow oil. The sample was loaded onto a 340 g Biotage® silica gel column from ethyl acetate and eluted with a gradient of 12-100% ethyl acetate in hexane to give 5.20 g of a colorless oil (54% yield). $^1$H NMR (500 MHz, CD$_2$Cl$_2$) δ 1.25-2.05 (m, 10H), 2.35 (s, 3H), 4.17 (m, 1H). The aromatic region of the spectrum showed only traces of non-deuterated product.

Step 2. Preparation of the [L$_2$IrCl]$_2$ Compound

Combined IrCl$_3$(H$_2$O)$_3$ (1.43 g, 4.06 mmol) and 18 mL water and stirred to dissolve. Added 1-cyclohexyl-3-methyl-5-phenyl-1H-1,2,4-triazole-d$_5$ (2.50 g, 10.2 mmole) and 56 mL of 2-ethoxyethanol, purged the mixture with nitrogen, and heated to reflux overnight. The mixture was cooled and 51 mL of water was added to help precipitate the product. The mixture was stirred for 0.5 h and then the solids were collected by filtration and washed on the filter 3× with 67 mL of water and air dried to afford a yellow solid. The solid was dried overnight under high vacuum to afford 2.45 g of a yellow solid (92% yield). $^1$H NMR (500 MHz, CD$_2$Cl$_2$) δ 1.39-2.30 (m, 13H), 4.76 (m, 1H). A low intensity singlet at 7.46 ppm, corresponding to the aromatic position ortho to the triazole and integrating for ~0.4H, was also observed.

Step 3. Preparation of the L$_2$Ir(OTf) Compound

The [L$_2$IrCl]$_2$ compound from step 2 (2.44 g, 1.70 mmol) was dissolved in 26 mL dichloromethane. Silver trifluoromethanesulfonate (0.87 g, 3.40 mmol) was added and the reaction mixture heated at reflux for 4 h. After cooling to room temperature, the reaction mixture was filtered through a chromatographic column and washed several times with dichloromethane. The filtrate was concentrated to dryness and the resulting green foam was taken up in methanol. The methanol mixture was filtered through another column, which was washed several times with methanol. The methanol filtrate was concentrated to give a dark yellow solid, which was washed with pentane on a frit and dried to afford 2.71 g of a yellow solid (96% yield). $^1$H NMR (500 MHz, CD$_2$Cl$_2$) showed broad peaks: δ 1.5-2.2 (m, 10H), 2.5 (s, 3H), 4.7 (m, 1H). A low intensity singlet at 7.3 ppm, corresponding to the aromatic position ortho to the triazole and integrating for ~0.4H, was also observed.

Step 4. Preparation of the IrL$_3$ Compound

The L$_2$Ir(OTf) compound above (2.70 g, 3.25 mmol) was dissolved in 2-ethoxyethanol (84 mL). To this stirred solution was added the ligand 1-cyclohexyl-3-methyl-5-phenyl-1H-1,2,4-triazole-d$_5$ (1.60 g, 6.50 mmol). The reaction mixture was heated to 120° C. and stirred for 3.5 h. A yellow precipitate formed gradually. It was then cooled to room temperature and the precipitate filtered off and washed with a minimum amount of 2-ethoxyethanol and several times with pentane. It was dried under vacuum to afford 0.79 g of a yellow solid (yield=26%). This material was purified by chromatography on a 340 g Biotage® silica gel column. The sample was loaded on the column from dichloromethane and eluted with a gradient of 5-40% ethyl acetate in hexane. The main fractions were combined and concentrated to afford 0.77 g of compound B2 as a yellow solid. $^1$H NMR (500 MHz, CD$_2$Cl$_2$) δ 1.25-2.15 (m, 13H), 4.62 (m, 1H). A singlet at 7.53 ppm, corresponding to the aromatic position ortho to the triazole and integrating for ~0.15H, was also observed. UPLC in isopropanol/water indicated a purity of 99.95%.

Synthesis Example 3

This example illustrates the preparation of Compound B3.

Step 1. Preparation of 5-([1,1'-biphenyl]-3-yl)-1-cyclohexyl-3-methyl-1H-1,2,4-triazole 3-phenylbenzoic acid (8.33 g, 42.0 mmol) was dissolved in anhydrous DMF (150 mL). To this stirred solution was added 2-(7-Aza-1 H-Benzotriazole-1-yl)-1,1,3,3-tetramethyluronium hexafluorophosphate (17.6 g, 46.2 mmol) followed by acetamidine hydrochloride (5.96 g, 63.0 mmol) and diisopropylethylamine (21.5 g, 166.2 mmol). The resulting solution was stirred under nitrogen for 18 h at room temperature. Cyclohexylhydrazine hydrochloride (9.49 g, 63.0 mmol) was then added, followed by acetic acid (24.0 mL). The resulting mixture was heated to 90° C. for a total of 6 h. After cooling to room temperature, the mixture was diluted with 800 mL of ethyl acetate and stirred with excess aqueous sodium bicarbonate. The organic layer was separated and the aqueous layer extracted again with ethyl acetate. The organic layers were combined and washed three times with water, dried (MgSO$_4$), and concentrated under vacuum to afford 15.3 g of a viscous amber-colored oil. TLC indicated the presence of two products, with the major component having the faster Rf. A portion of the crude product (7.52 g) was loaded onto a 340 g Biotage® silica gel column from warm methylene chloride and eluted with a gradient of 12-100% ethyl acetate in hexane. The faster moving, major product was isolated by combining the major fractions and concentrating under vacuum to afford 5-([1,1'-biphenyl]-3-yl)-1-cyclohexyl-3-methyl-1H-1,2,4-triazole as an off-white solid (4.82 grams, 74% yield). $^1$H NMR (500 MHz, CD$_2$Cl$_2$) δ 1.3-2.2 (m, 10H), 2.4 (s, 3H), 4.3 (m, 1H), 7.4-7.8 (m, 9H). The slower moving, minor side-product was isolated by combining and drying the minor fractions to afford 1.74 g of a white solid. Its $^1$H NMR spectrum was consistent with the primary amide [1,1'-biphenyl]-3-carboxamide: (500 MHz, CD$_2$Cl$_2$) δ 5.5-6.5 (v. br, 2H), 7.4-8.2 (m, 9H).

Step 2. Preparation of the [L$_2$IrCl]$_2$ Compound

Combined IrCl$_3$(H$_2$O)$_3$ (1.32 g, 3.75 mmol) and 17 mL water and stirred to dissolve. Added 5-([1,1'-biphenyl]-3-yl)-1-cyclohexyl-3-methyl-1H-1,2,4-triazole (2.95 g, 9.30 mmole) and 52 mL of 2-ethoxyethanol, purged the mixture with nitrogen, and heated to reflux for overnight (internal temperature of 102° C.). The mixture was cooled and 47 mL of water was added to help precipitate the product. The mixture was stirred for 0.5 h and then the solids were collected by filtration and washed on the filter 3× with 47 mL of water, once with methanol, and air dried to afford 3.02 g a yellow solid. The solid was dried overnight under high vacuum to afford 0.59 g of a yellow solid (93% yield). $^1$H NMR (500 MHz, CD$_2$Cl$_2$) δ 1.40-2.40 (m, 13H), 4.80 (m, 1H), 6.32 (d, 1H), 7.0 (dd, 1H), 7.30 (t, 1H), 7.41 (t, 2H), 7.51 (d, 2H), 7.70 (s, 1H).

Step 3. Preparation of the L$_2$Ir(OTf) Compound

The [L$_2$IrCl]$_2$ from step 2 (3.02 g, 1.75 mmol) was dissolved in 27 mL dichloromethane. Silver trifluoromethanesulfonate (0.902 g, 3.51 mmol) was added and the mixture was heated at reflux for 3 h. AgCl was observed to precipitate even before heating. The reaction mixture was cooled to room temperature, filtered through a chromatography column and concentrated to dryness to afford 3.25 g of a yellow solid (95% yield). $^1$H NMR (500 MHz, CD$_2$Cl$_2$) showed broad peaks: δ 1.4-2.3 (m, 10H), 2.7 (s, 3H), 4.7 (m, 1H), 6.4 (br, 1H), 7.1 (d, 1H), 7.3 (t, 1H), 7.4 (t, 2H), 7.5 (d, 2H), 7.7 (5, 1H).

Step 4. Preparation of the IrL$_3$ Compound

The L$_2$Ir(OTf) compound from step 3 (0.3.22 g, 3.31 mmol) was partially dissolved in 2-ethoxyethanol (86 mL). To this stirred solution was added the ligand 5-([1,1'-biphenyl]-3-yl)-1-cyclohexyl-3-methyl-1H-1,2,4-triazole (1.81 g, 5.70 mmol). The reaction mixture was heated to 120-122° C. and stirred for 71 h. It was then cooled to room temperature and the precipitate filtered off and washed with 2-ethoxyethanol and pentane. It was dried under vacuum to afford 0.41 g of a tan solid. The filtrate was diluted with 110 mL of water forming a yellow precipitate. This precipitate was filtered off and washed several times with water and once with methanol and dried to afford 2.85 g of a yellow solid. The yellow solid dissolved in methylene chloride and loaded onto a 34 g silica gel cartridge and chromatographed on a 340 g Biotage® silica gel column. The eluent was 1-8% ethyl acetate in methylene chloride. The main fractions were combined and concentrated to afford 1.00 g of compound B3 as a yellow solid (26% yield). $^1$H NMR (500 MHz, CD$_2$Cl$_2$) δ 1.1-2.2.1 (m, 13H), 4.72 (m, 1H), 6.79 (d, 1H), 7.02 (dd, 1H), 7.22 (t, 1H), 7.34 (t, 2H), 7.52 (d, 2H), 7.70 (s, 1H). UPLC in isopropanol/water indicated a purity of 99.6%.

Synthesis Example 4

This example illustrates the preparation of Compound B4.

Step 1. Preparation of
1-mesityl-3-methyl-5-phenyl-1H[1,2,4]-triazole

N-Benzoylacetamidine was prepared according to Cook, M. J.; et. al. *J. Chem. Soc. Perkin II* 1974, 546, and 5.93 g (36.6 mmol) was dissolved in 120 mL anhydrous DMF. 2,4,6-trimethylphenylhydrazine hydrochloride (9.46 g, 50.7 mmol) was added followed by 21 mL of acetic acid. The mixture was heated to 90° C. for 3 h. After cooling to room temperature the reaction mixture was placed in a 1 liter beaker and an aqueous saturated solution of NaHCO$_3$ was added slowly until the mixture stopped foaming and became basic (~800 mL). The mixture was extracted with 2×300 mL ethyl acetate. The extracts were washed with water (3×800 mL), brine (2×800 mL) and then dried over MgSO$_4$, filtered, and evaporated to give 11.51 g crude product. Chromatography on a 340 g Biotage® silica gel column eluting with a gradient of 7-59% ethyl acetate in hexane gave 7.77 g (77% yield) pure product. $^1$H NMR (400 MHz, CDCl$_3$) δ 1.90 (s, 6H), 2.36 (s, 3H), 2.46 (s, 3H), 6.99 (m, 2H), 7.28 (t, 2H), 7.35 (t, 1H), 7.47 (d, 1H).

Step 2. Preparation of the [L$_2$IrCl]$_2$ Compound

Combined IrCl$_3$(H$_2$O)$_3$ (2.47 g, 7.00 mmol) and 33 mL water and stirred to dissolve. Added 1-mesityl-3-methyl-5-phenyl-1H-[1,2,4]triazole (4.27 g, 15.4 mmol) and 100 mL of 2-ethoxyethanol, purged the mixture with nitrogen, and heated to reflux for 16 h. The mixture was cooled and 120 mL of water was added to help precipitate the product. The solids were collected by filtration and washed on the filter 3× with water followed by 2× with methanol. The yellow solid was dried by pulling nitrogen through the filter. The dried solid was dissolved in dichloromethane, dried over MgSO$_4$, filtered and evaporated to give 4.86 g bright yellow solid (89% yield). $^1$H NMR (400 MHz, CD$_2$Cl$_2$) δ 1.92 (s, 3H), 2.24 (s, 3H), 2.43 (s, 3H), 2.62 (s, 3H), 6.27 (d, 1H), 6.34 (d, 1H), 6.55 (t, 1H), 6.71 (t, 1H), 7.07 (s, 1H), 7.16 (s, 1H).

Step 3. Preparation of the L$_2$Ir(OTf) Compound

The [L$_2$IrCl]$_2$ compound from step 2 (4.86 g, 6.23 mmol) was dissolved in 100 mL of 95:5 dichloromethane/methanol. Silver trifluoromethanesulfonate (1.60 g, 6.23 mmol) was added and the mixture was protected from light and stirred at room temperature for 16 h. The solvents were evaporated on a rotary evaporator and the mixture was extracted with methanol and filtered through a chromatography column to remove the AgCl. The column was washed with methanol until the filtrates were colorless. The combined filtrates were evaporated and triturated with hexanes to give a light yellow solid that was collected on a filter and dried under a nitrogen stream to give 5.48 g (98% yield). ¹H NMR (400 MHz, CD₂Cl₂) δ 2.02 (s, 3H), 2.08 (s, 3H), 2.43 (s, 3H), 2.75 (s, 3H), 6.34 (d, 1H), 6.38 (bd, 1H), 6.62 (t, 1H), 6.76 (t, 1H), 7.10 (s, 1H), 7.14 (s, 1H).

Step 4. Preparation of the IrL₃ Compound

L₂Ir(O₃SCF₃) (5.47 g, 6.12 mmol) and 1-mesityl-3-methyl-5-phenyl-1H-[1,2,4]triazole (3.39 g, 12.2 mmol) were combined in 75 mL of n-propanol, sparged with nitrogen, and heated to reflux for 16 h. After cooling to room temperature the solids were collected by filtration and washed with minimal propanol 2× followed by minimal hexanes 2×. Vacuum drying gave 3.56 g yellow solid (57% yield). The sample was loaded onto a 340 g Biotage silica gel column from dichloromethane. The sample was eluted with a gradient of 6-50% ethyl acetate in hexanes. The collected fractions were cooled to 0° C. overnight and 1.05 g yellow solid crystallized in the more concentrated collection bottles. ¹H NMR (CD₂Cl₂) showed unidentified aliphatic impurities with a doublet at 0.98 ppm and a triplet at 0.87 ppm. The material was rechromatographed on a 100 g Biotage® silica gel column (loaded from dichloromethane solution) using a gradient of 1-10% ethyl acetate in dichloromethane. Isolated 0.65 g of compound B4 as a yellow solid (10% yield). UPLC on a BEH Phenyl column (1.7 uM, 2.1×50 mm) using 70:30 water/IPA with no formic acid indicated a purity of 99.95%. ¹H NMR (400 MHz, CD₂Cl₂) δ 1.77 (s, 3H), 2.07 (s, 3H), 2.13 (s, 3H), 2.42 (s, 3H), 6.45 (d, 1H), 6.52 (d, 1H), 6.56 (t, 1H), 6.64 (t, 1H), 7.05 (s, 1H), 7.11 (s, 1H).

Device Examples

These examples demonstrate the fabrication and performance of OLED devices.

(1) Materials

HIJ-1 is an electrically conductive polymer doped with a polymeric fluorinated sulfonic acid. Such materials have been described in, for example, published U.S. patent applications US 2004/0102577, US 2004/0127637, US 2005/0205860, and published PCT application WO 2009/018009.

HT-1 is a triarylamine-contain ng polymer. Such materials have been described in, for example, published PCT application WO2009/067419.

Host-1 the carbazole derivative shown below.

ET-1 is a metal quinolate complex.

Comparative compounds A1 and A2, shown below, were made according to the procedure in U.S. Pat. No. 7,659,010, and Lo. S.-C. at al. *Chem. Mater.* 2006, 18, 5119.

Comparative A1

Comparative A2

The devices had the following structure on a glass substrate:
  anode=Indium Tin Oxide (ITO), 50 nm
  hole injection layer=HIJ-1 (50 nm)
  hole transport layer=HT-1 (20 nm)
  photoactive layer, discussed below=100:14 Host-1:dopant (43 nm);
  anti-quenching layer=Host-1 (10 nm)
  electron transport layer=ET-1 (10 nm)
  electron injection layer/cathode=CsF/Al (1/100 nm)

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a hole transport solution, and then heated to remove solvent. The substrates were masked and placed in a vacuum chamber. The photoactive layer, the electron transport layer and the anti-quenching layer were deposited by thermal evaporation, followed by a layer of CsF. Masks were then changed in vacuo and a layer of Al was deposited by thermal evaporation. The chamber was vented, and the devices were encapsulated using a glass lid, desiccant, and UV curable epoxy.

(3) Device Characterization

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The color coordinates were determined using either a Minolta CS-100 meter or a Photoresearch PR-705 meter.

Examples 1-4 and Comparative Examples A1 and A2

These examples illustrate the use of compounds having Formula I as the light emitting material in a device.

The materials used and the results are given in Table 1 below.

TABLE 1

Device results

| Example | Dopant | $R^1$ | $R^2$ | $R^3$ | Peak Emission (nm) | CIE(x, y) | EQE (%) |
|---|---|---|---|---|---|---|---|
| Comp. A1 | A1 | Me | Pr | H | 454 | (.153, .215) | 11.7 |
| Comp. A2 | A2 | Me | Me | H | 459 | (.153, .217) | 14.4 |
| 1 | B1 | Cyclohexyl | Me | H | 460 | (.162, .284) | 17 |
| 2 | B2 | Cyclohexyl | Me | D | 459 | (.151, .204) | 23 |
| 3 | B3 | Cyclohexyl | Me | Ph | 472 | (.162, .317) | 22 |
| 4 | B4 | Mesityl | Me | H | 458 | (.15, .197) | 16 |

All data @ 1000 nits. E.Q.E. is the external quantum efficiency; CIE(x, y) are the x and y color coordinates according to the C.I.E. chromaticity scale (Commission Internationale de L'Eclairage, 1931).

It can be seen from Table 1 that the efficiency is significantly increased when the compound of Formula I is present as the dopant.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A compound having Formula I wherein:
  $R^1$ is selected from the group consisting of phenyl, napthyl, and deuterated analogs thereof;
  $R^2$ is selected from the group consisting of alkyl, and deuterated alkyl;
  $R^3$ is selected from the group consisting of H, D, aryl, and deuterated aryl; and
  $R^4$-$R^6$ are the same or different and are selected from the group consisting of H, D, alkyl, and deuterated alkyl.

2. A compound having Formula I wherein:
  R1 and R3 are the same or different and are aryl groups or deuterated aryl groups;
  $R^2$ is selected from the group consisting of alkyl, and deuterated alkyl; and
  $R^4$-$R^6$ are the same or different and are selected from the group consisting of alkyl and deuterated alkyl.

3. A compound having Formula I wherein:
R¹ is selected from the group consisting of secondary alkyls, tertiary alkyls, and deuterated analogs thereof;
R2 is selected from the group consisting of alkyl, and deuterated alkyl; and
R³-R⁶ are all D.

4. A compound selected from compound B1 through B12

B1

B2

B3

B4

B5

B6

B7

B8

* * * * *